(12) United States Patent
Gournay et al.

(10) Patent No.: US 6,475,218 B2
(45) Date of Patent: Nov. 5, 2002

(54) SPINAL IMPLANT FOR AN OSTEOSYNTHESIS DEVICE

(75) Inventors: José Gournay, Dammartin en Goele; Stéphan Chojnicki, Villepinte, both of (FR)

(73) Assignee: Sofamor, S.N.C., Roissy CDG Cedex (FR)

( * ) Notice: Subject to any disclaimer, the term of this patent is extended or adjusted under 35 U.S.C. 154(b) by 0 days.

(21) Appl. No.: 09/897,265

(22) Filed: Jul. 2, 2001

(65) Prior Publication Data
US 2002/0013585 A1 Jan. 31, 2002

(51) Int. Cl.[7] .............................................. A61B 17/56
(52) U.S. Cl. ........................ 606/61; 606/73; 623/17.16
(58) Field of Search .............................. 606/61, 71, 60, 606/72, 69, 70, 73; 623/17.11, 17.16

(56) References Cited

U.S. PATENT DOCUMENTS

| 5,005,562 A | | 4/1991 | Cotrel | 128/69 |
|---|---|---|---|---|
| 5,257,993 A | | 11/1993 | Asher et al. | 606/61 |
| 5,534,001 A | | 7/1996 | Schlapfer et al. | 606/61 |
| 5,549,608 A | | 8/1996 | Errico et al. | 606/61 |
| 5,603,714 A | * | 2/1997 | Kaneda et al. | |
| 5,651,789 A | | 7/1997 | Cotrel | 606/61 |
| 5,669,911 A | | 9/1997 | Errico et al. | 606/61 |
| 5,690,630 A | | 11/1997 | Errico et al. | 606/61 |
| 5,697,929 A | | 12/1997 | Mellinger | 606/61 |
| 5,888,221 A | * | 3/1999 | Gelbard | |
| 6,004,349 A | | 12/1999 | Jackson | 623/17 |
| 6,056,753 A | | 5/2000 | Jackson | 606/73 |
| 6,063,089 A | | 5/2000 | Errico et al. | 606/61 |
| 6,063,090 A | | 5/2000 | Schlapfer | 606/61 |
| 6,179,841 B1 | | 1/2001 | Jackson | 606/73 |
| 6,224,596 B1 | | 5/2001 | Jackson | 606/61 |
| 6,224,598 B1 | | 5/2001 | Jackson | 606/61 |
| 6,248,105 B1 | * | 6/2001 | Schlapfer | |
| 6,296,642 B1 | * | 10/2001 | Morrisson et al. | |

FOREIGN PATENT DOCUMENTS

JP  08336548  12/1996

* cited by examiner

Primary Examiner—Pedro Philogene
(74) Attorney, Agent, or Firm—Woodard, Emhardt, Naughton, Moriarty & McNett

(57) ABSTRACT

A spinal implant for an osteosynthesis device having a bone anchorage portion, a connector portion adapted for connection to an elongate rod, an extension portion extending from the connector portion, and a threaded fastener operable to secure the implant to the elongate rod. The connector portion includes a pair of flanges extending axially from the anchorage portion and spaced apart to define a channel for receiving the elongate rod therein. The extension portion includes a first segment extending axially from one of the flanges and a second segment extending transversely from the first segment toward the other of the flanges so as to define a transverse opening capable of receiving the elongate rod therethrough. The fastener is advanced along a continuous thread extending between the extension portion and the opposing flanges to secure the elongate rod within the channel. In one embodiment, the extension portion is selectively separable from the connector portion.

45 Claims, 3 Drawing Sheets

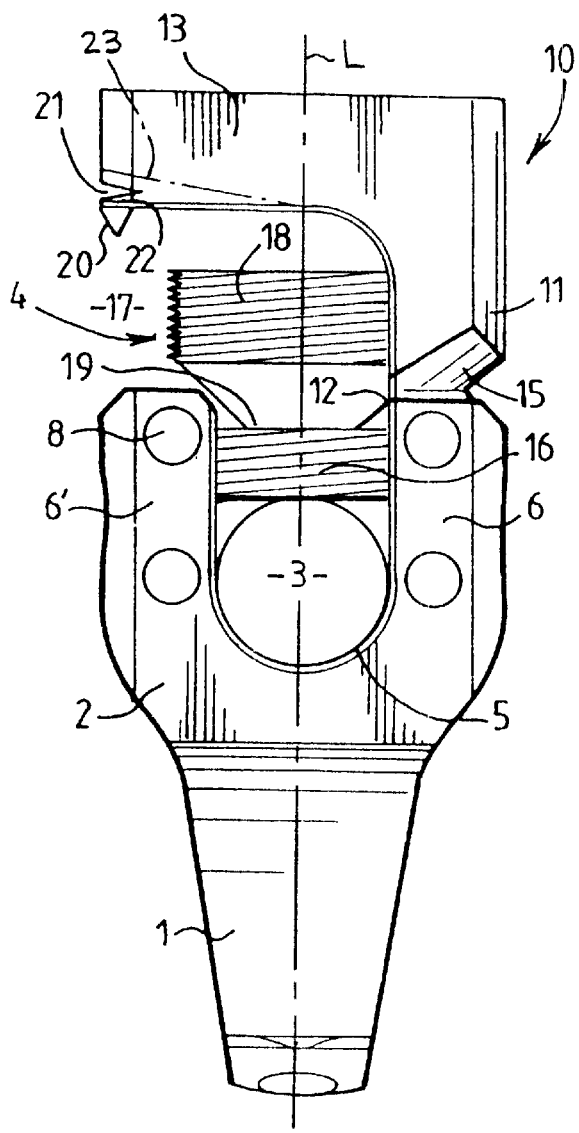
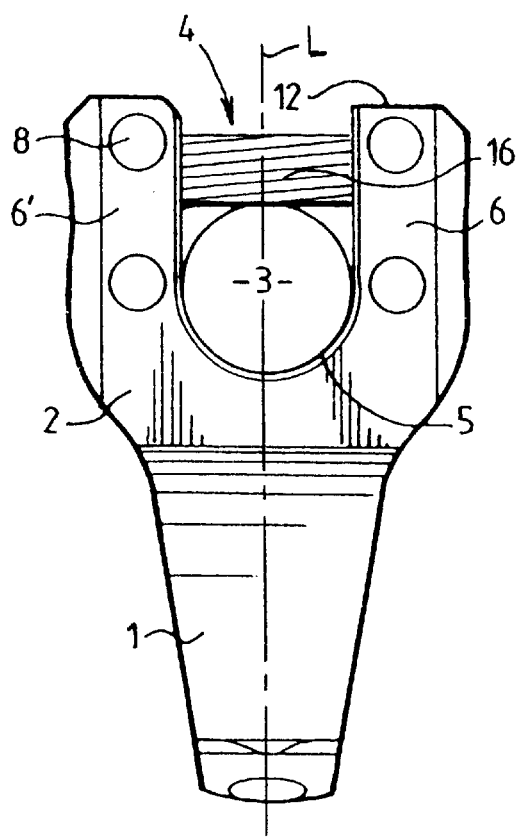
FIG. 3
FIG. 4

SPINAL IMPLANT FOR AN OSTEOSYNTHESIS DEVICE

The present application claims the benefit of French Patent Application No. 00 08 535 filed Jun. 30, 2000, the contents of which are hereby expressly incorporated by reference.

FIELD OF THE INVENTION

The present invention relates generally to a spinal implant for an osteosynthesis device, and more specifically, but not exclusively, relates to a spinal implant having a bone anchorage portion adapted to engage bone and a connector portion adapted to connect the spinal implant to an elongate rod positioned adjacent the spine.

BACKGROUND OF THE INVENTION

Prior spinal implants have been developed that effectively anchor an elongate rod to vertebral bone. Such implants generally include a pair of opposing branches that form a U-shaped channel therebetween, with the U-shaped channel being sized to receive the elongate rod therein. The elongate rod is typically clamped within the U-shaped channel by way of a set screw that is threadingly engaged between the opposing branches of the implant that form the channel.

Spinal implants of the type described above have certain inherent disadvantages. For example, since the inner threads formed along the opposing branches of the implant are interrupted by the U-shaped channel, the likelihood of cross-threading the outer threads of the set screw with the inner threads of the opposing branches is significant. To prevent cross-threading, extraordinary care must be taken by the surgeon to ensure that the set screw is axially aligned with the threaded opening formed between the opposing branches prior to initiating threading engagement. If cross threading occurs, the surgeon must disengage the set screw from the threaded opening and repeat the alignment and thread initiating process. Worse yet, the implant may become damaged by the cross-threading to such an extent as to render the implant and/or the set screw unusable. Additionally, since the elongate rod must typically be inserted into the channel prior to threading the set screw into the threaded opening between the side branches, the set screw cannot be pre-threaded into the threads of the connector portion prior to implanting the spinal implant within the patient's body. This leads to significant "fiddle factor" by the surgeon during the surgical procedure.

Thus, there is a general need in the industry to provide an improved spinal implant for an osteosynthesis device. The present invention meets this need and provides other benefits and advantages in a novel and unobvious manner.

SUMMARY OF THE INVENTION

The present invention relates generally to a spinal implant for an osteosynthesis device. While the actual nature of the invention covered herein can only be determined with reference to the claims appended hereto, certain forms of the invention that are characteristic of the preferred embodiments disclosed herein are described briefly below.

In one form of the present invention, a spinal implant is provided having a bone anchorage portion, a connector portion including first and second flanges that are spaced apart to define a channel sized to receive an elongate member therein, an extension portion including a first portion extending axially from the first flange and a second portion extending transversely from the first portion and toward the second flange, and a fastener operable to advance along the first and second portions of the extension portion and into engagement with the first and second flanges to secure the elongate member within the channel.

In another form of the present invention, a spinal implant is provided having a bone anchorage portion adapted for engagement with a vertebral body, a connector portion extending from the anchorage portion and being adapted for connection to an elongate member, an extension portion extending from the connector portion and being selectively removable therefrom, and a fastener operable to advance along the extension portion and the connector portion and into engagement with the elongate member to operatively connect the connector portion to the elongate member.

In still another form of the present invention, a spinal implant is provided having an anchoring portion adapted to engage bone and a body portion adapted for fixation to an elongate rod. The body portion includes a channel delimited by a pair of opposing side branches which define a first threading, and a continuation including a first portion extending axially from one of the side branches and a second portion extending laterally from the first portion toward the other of the side branches, with the continuation defining a second threading in continuity with the first threading. The implant further includes means for clamping the elongate rod within the channel, which cooperates with the first and second threadings to advance along the body portion and into engagement with the elongate rod to clamp the elongate rod within the channel.

It is one object of the present invention to provide an improved spinal implant for an osteosynthesis device.

Further objects, features, advantages, benefits, and aspects of the present invention will become apparent from the drawings and description contained herein.

BRIEF DESCRIPTION OF THE DRAWINGS

FIG. 2a is a front view of the spinal implant depicted in FIG. 1.

FIG. 2b is a longitudinal cross-sectional view of the spinal implant depicted in FIG. 2a.

FIG. 3 is a front view of the spinal implant depicted in FIG. 1, illustrating a first operational configuration of the implant in which an elongate rod is secured within the connecting portion of the implant by a set screw.

FIG. 4 is a front view of the spinal implant depicted in FIG. 1, illustrating a second operational configuration of the implant in which an elongate rod is secured within the connecting portion of the implant by a set screw, and also illustrating the subsequent removal of a portion of the implant body and a portion of the set screw.

FIG. 5b is a longitudinal cross-sectional view of the spinal implant depicted in FIG. 5a.

DESCRIPTION OF THE ILLUSTRATED EMBODIMENTS

Figure 1:
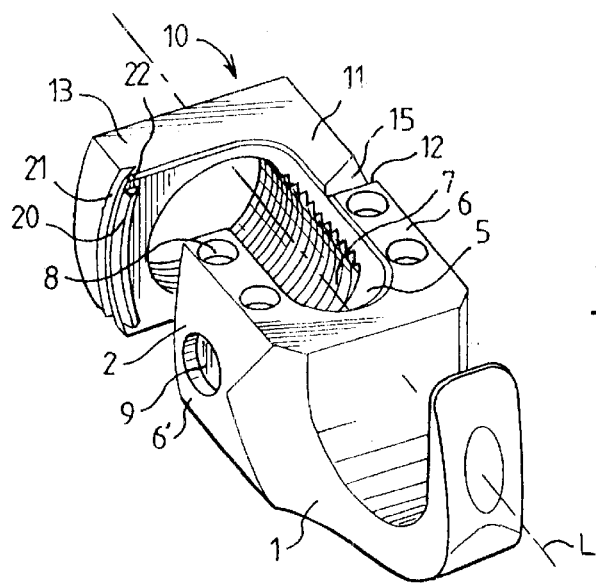
FIG. 1 is a perspective view of a spinal implant according to one form of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figures 2A, 2B:
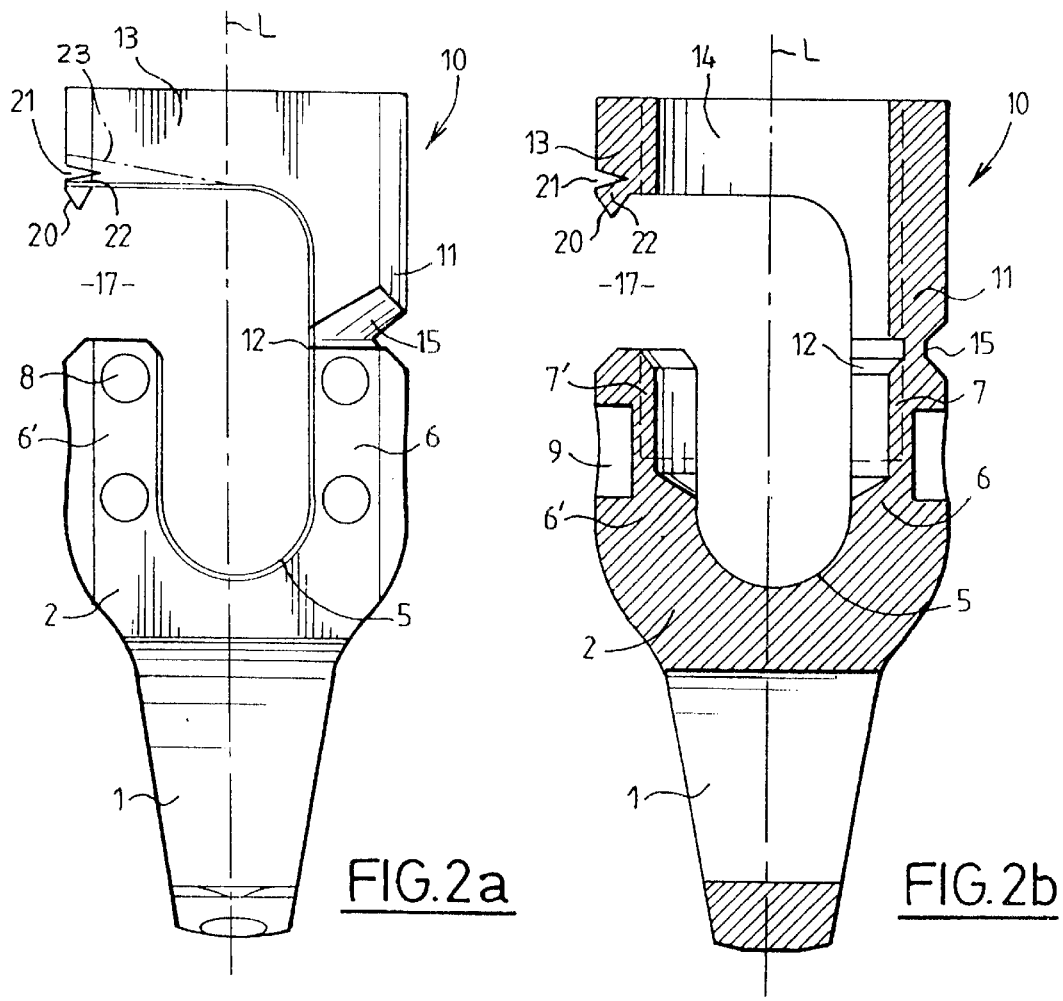

Referring to FIGS. 1–4, shown therein is a spinal implant according to one form of the present invention. The spinal implant extends along a longitudinal axis L and is generally comprised of a bone anchorage portion 1 and a connector portion 2 adapted to connect the spinal implant to an elongate rod 3 by way of a fastener or plug 4 (as shown in FIGS. 3 and 4).

In the illustrated embodiment, the bone anchorage portion 1 is comprised of a hook that is configured to extend about a portion of a bone, such as, for example, a portion of a vertebral body. However, it should be understood that the bone anchorage portion 1 can take on other configurations as well, such as, for example, a bone screw that is configured to penetrate a vertebral body. It should also be understood that the outer surface of the elongate rod 3 can be smooth or may alternatively be roughened to aid in securing the connector portion 2 to the rod 3. Similarly, the surface of fastener 4 that engages the rod 3 may also be roughened to aid in securing the connector portion 2 to the rod 3. Such roughened surfaces have the effect of reducing the likelihood of rotational or lateral sliding of the rod 3 relative to the connector portion 2 once the fastener 4 is tightened against the rod 3. Although the rod 3 is illustrated as having a generally circular cross-section, it should be understood that other shapes and configurations of rod 3 are also contemplated as would occur to one of ordinary skill in the art.

A lower section of the connector portion 2 extends directly from the bone anchorage portion 1 and defines a U-shaped channel 5 sized to receive the elongate rod 3 therein. The U-shaped channel 5 is delimited laterally by a pair of opposing side branches or flanges 6, 6'. The inwardly facing surfaces of flanges 6, 6' define a series of inner threads 7, 7', respectively. The threads 7, 7' are preferably formed in a single threading operation so as to provide uniformity and continuity therebetween to ensure proper threading engagement with the fastener 4. The lower section of connector portion 2 also includes a number of recesses 8, 9 disposed about its perimeter which allow the surgeon to securely grip and manipulate the spinal implant using suitable instrumentation (not shown) known to those of skill in the art.

An upper section of the connector portion 2 extends from the lower section so as to define a continuation or extension 10 of the spinal implant. The extension 10 includes a first portion 11 extending axially from the upper end 12 of flange 6 in substantially the same direction as branch 6. However, it should be understood that the axial portion 11 of extension 10 could alternatively extend from flange 6'. Preferably, but not necessarily, the axial portion 11 is aligned generally parallel to flange 6'. The extension 10 also includes a second portion 13 extending transversely from the first portion 11, and toward flange 6' so as to position the second portion 13 generally above the U-shaped channel 5. Preferably, but not necessarily, the transverse portion 13 extends from the axial portion 11 in a generally perpendicular direction.

The transverse portion 13 and the axial portion 11 cooperate to define a threaded opening 14 that is substantially aligned with the threaded portion of the U-shaped channel 5, and which includes a series of inner threads similar to those of threads 7, 7' which are also configured to threadingly engage the fastener 4. Preferably, the threads of the threaded opening 14 and the threads 7, 7' are formed in a single threading operation so as to provide uniformity and continuity therebetween. In this manner, a continuous thread is formed that extends through the opening 14 in the transverse portion 13 of extension 10, along the axial portion 11 of extension 10, and between the opposing flanges 6, 6'. As a result, the fastener 4 may be continually threaded through the extension 10 and into engagement between the flanges 6, 6' and into abutment against the elongate rod 3.

In one embodiment of the present invention, a notch 15 is machined along an outer surface of the spinal implant at a position adjacent the upper surface 12 of flange 6. The notch 15 provides the spinal implant with an area of reduced outer cross-section so as to define a region of reduced strength. In this manner, notch 15 serves as a fracture initiator which allows the extension 10 to be controllably and selectively separated from flange 6 of connector portion 2. It should be understood, however, that other means may be provided to allow the extension 10 to be controllably and selectively separated from the remainder of the implant. For example, the extension 10 could alternatively be mechanically attached to the remainder of the implant by way of a number of pins. Alternatively, the extension 10 could be mechanically attached to the remainder of the implant by way of a tongue-and-groove arrangement, such as, for example, a dovetail configuration or by a tenon and mortise configuration. Alternatively, adhesive bonding could be used to attach the extension 10 to the remainder of the implant. Other means for attaching the extension 10 to the remainder of the implant may also be used as would occur to one of ordinary skill in the art.

Having described the general features of the spinal implant, a method of using the spinal implant in association with an osteosynthesis device will now be described according to one embodiment of the present invention. Prior to implantation of the spinal implant, the threaded fastener 4 is preferably initially threaded into the threaded opening 14 of extension 10. The lower portion 16 of fastener 4 is threaded through opening 14 in the lateral portion 13, but with care being taken not to protrude the lower surface of fastener 4 beyond the lower surface of lateral portion 13. In this manner, the fastener 4 is provisionally secured to the spinal implant so that it cannot be inadvertently or unintentionally removed therefrom, and without in any way restricting the lateral opening 17 through which the elongate rod 3 is to be inserted. Importantly, the initial threading engagement of the fastener 4 with the lateral portion 13 of extension 10 is aided by the fact that threads are formed about the entire perimeter of engagement of opening 14. Such would not be the case if the fastener 4 were to be threaded directly between the opposing flanges 6, 6' since threads 7, 7' are interrupted by the U-shaped channel 5.

The spinal implant may then be anchored to the spine by positioning a portion of the vertebral body within the hook 1, the details of which would be apparent to one of ordinary skill in the art. The elongate rod 3 is then inserted laterally through the opening 17 defined between the lateral portion 13 of extension 10 and flange 6' of connector portion 2. The elongate rod 3 may then be axially displaced along the U-shaped channel 5. The fastener 4 is then threaded the remainder of the way through lateral portion 13 of extension 10, along the axial portion 11, and into threaded engagement with threads 7, 7' of flanges 6, 6'. Further threading of fastener 4 between flanges 6, 6' will cause the lower portion 16 of fastener 4 to engage the elongate rod 3 and press the rod 3 tightly against the bottom of the U-shaped channel 5 (FIG. 3).

As shown in FIG. 3, in one embodiment of the invention, the fastener 4 is a set screw that includes an upper portion 18 that is coaxial with the lower portion 16 and which is controllably and selectively separable from the lower portion 16. In one embodiment, a notch is formed adjacent the location where the lower and upper portions 16, 18 of the set screw 4 interface. The notch effectively separates the lower and upper portions 16, 18 of set screw 4 by an incipient break line 19 which provides a region of reduced strength that allows the upper portion 18 to be controllably and selectively separated from the lower portion 16 (FIG. 4). It should be understood, however, that other means may be provided for controllably and selectively separating the upper portion 18 from the lower portion 16, including those means described above with regard to the selective separation of extension 10 from the remainder of the spinal implant.

As shown in FIG. 3, in its initial state, the set screw 4 has a relatively lengthy axial dimension. Preferably, the axial length of set screw 4 is such that set screw 4 is always in threading engagement with either or both of the threaded opening 14 in lateral position 13 or the threads 7, 7' of flange 6, 6'. The initial axial length of set screw 4, coupled with the provision of continuous thread extending through the axial and lateral portions 11, 13 of extension 10, aid in guiding the set screw 4 through the implant and into engagement with rod 3. As a result, the elongate rod 3 may be efficiently and reliably engaged against the bottom of the U-shaped channel 5. Prior to removing extension 10 from the remainder of the implant, the lower portion 16 of set screw 4 is preferably entirely disposed between the opposing flanges 6, 6' of connector portion 2 (i.e., the upper surface of lower portion 16 is at or below the upper surface 12 of flanges 6, 6').

At this point, the extension 10 is separated from the lower section of connector portion 2. In one embodiment, the surgeon may initiate such separation by using forceps to break the extension 10 along the contour of notch 15. If required, the surgeon may then further tighten the set screw 4 against the elongate rod 3 to additionally secure the rod 3 against the bottom of channel 5. When the tightening torque of set screw 4 reaches a predetermined level, the set screw 4 will rupture or fracture along the incipient break line 19 to thereby separate the upper portion 18 from the lower portion 16. In this manner, only the lower portion 16 will remain in engagement with the spinal implant (See FIG. 4). As discussed above, the axial length of the lower portion 16 of set screw 4 is preferably sized such that the upper surface of lower portion 16 does not protrude beyond the upper ends 12 of opposing flanges 6, 6'. As a result, subsequent to the removal of extension 10 and the separation of the upper portion 18 from the lower portion 16, the spinal implant is provided with a relatively low profile (compare FIG. 4 to FIG. 3). Additionally, since the lower portion 16 of set screw 4 does not protrude beyond the upper ends 12 of opposing flanges 6, 6', the likelihood of injury to adjacent tissue by a sharp edge or point caused by the fracturing of set screw 4 is reduced.

In a further embodiment of the present invention, the lower surface of lateral portion 13 of extension 10 includes a protrusion or retention relief 20 which provides the lateral opening 17 with a width that is slightly less than the diameter of the elongate rod 3. In this manner, during the introduction of rod 3 through the lateral opening 17, pressure is exerted on the relief 20 which, in turn, slightly deforms the extension 10 to allow the rod 3 to be displaced through the lateral opening 17. Importantly, extension 10 must have sufficient resiliency to allow deformation of the lateral portion 13 in an upward direction without fracturing extension 10. Once the rod 3 is inserted through the opening 17 and positioned beyond the relief 20, the extension 10 will return or snap back to its original configuration. In this manner, the elongate rod 3 is provisionally maintained within the inner channel of the spinal implant, thereby reducing the risk of inadvertent or unintentional disengagement of rod 3 from connector portion 2. Moreover, by providing the relief 20, it is possible for the surgeon to position the spinal implant on the elongate rod 3 prior to introducing the osteosynthesis device into the patient's body, thereby further reducing the "fiddle factor" associated with the surgical procedure.

In another embodiment of the present invention, the required amount of flexion or deformation of extension 10 to allow the insertion of rod 3 through the lateral opening 17 is provided, at least in part, by the region of reduced strength associated with notch 15. Alternatively, a V-shaped notch 21 may be provided in the lateral portion 13 of extension 10 immediately adjacent the relief 20. The V-shaped notch 21 permits upward deflection of the lower lip 22 during insertion of the rod 3 through the lateral opening 17. In yet another embodiment, the deflectable lower lip 22 could itself constitute the retention relief which, in its initial position, would limit the width of opening 17 to a value slightly less than the diameter of rod 3. In still another embodiment, as most clearly shown in FIG. 2a, the inwardly facing surface of the lateral portion 13 of extension 10 could be provided with an inwardly tapering bevel 23. The bevel 23 would provide opening 17 with a narrowing width to aid in the introduction of rod 3 through lateral opening 17.

As discussed above, extension 10 may be controllably and selectively separated from the remainder of the implant. If the notch 15 is used to initiate such separation, the spinal implant is preferably formed as a single, unitary structure. However, it should be understood that the extension 10 can be formed separately from the remainder of the implant so as to define a two-piece structure. In this case, the two separate pieces are preferably secured to one another prior to the formation of the inner threads of the implant in order to provide a continuous and uniform screw thread. As discussed above, various means may be used to attach the extension 10 to the remainder of the implant. It should also be understood that the extension 10 need not necessarily be formed of the same material as the remainder of the implant. For example, the extension 10 may be formed of a non-metallic material, such as, for example, a polymer or a composite material, while the remainder of the implant may be formed of a biocompatible metallic material, such as, for example, titanium or stainless steel.

Figure 5A:
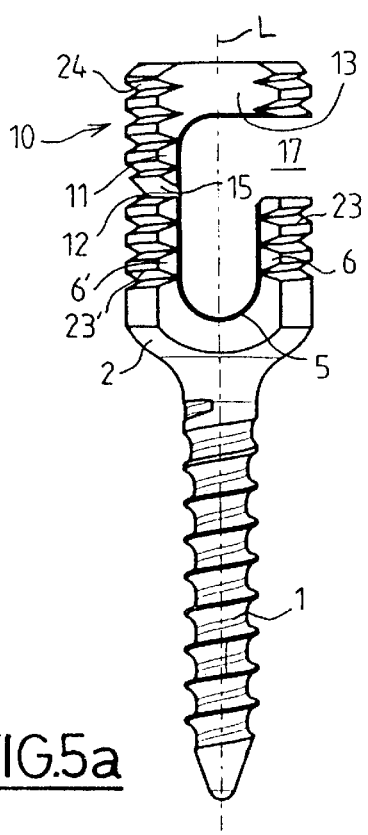
FIG. 5a is a front view of a spinal implant according to another form of the present invention.
Figure 5B:
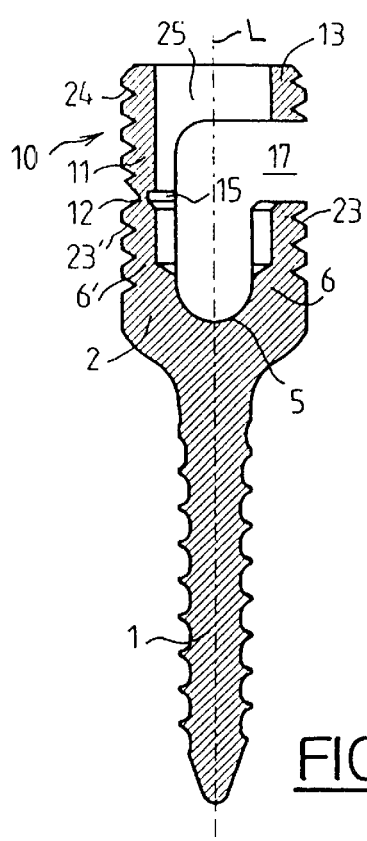
Figure 6:
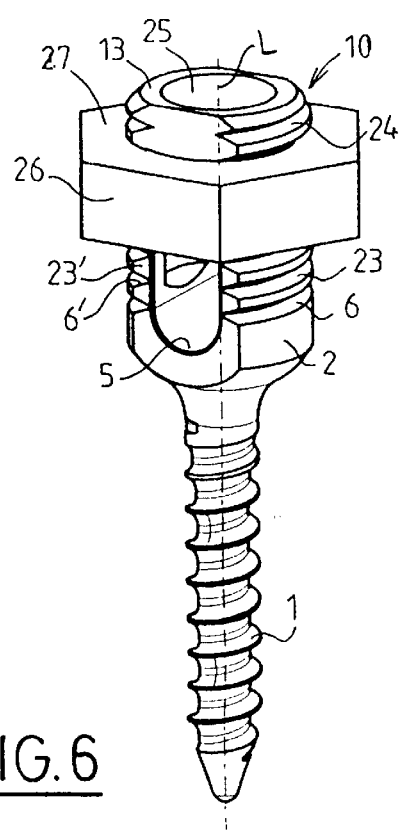
FIG. 6 is a perspective view of the spinal implant depicted in FIG. 5a, illustrating a first operational configuration of the implant in which a nut is used to secure an elongate rod within the connecting portion of the implant.
Figure 7:
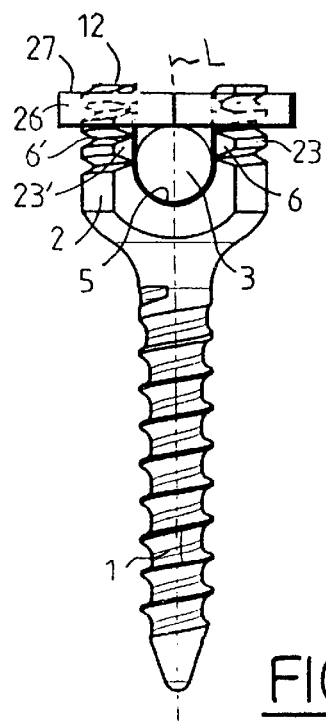
FIG. 7 is a front view of the spinal implant depicted in FIG. 5a, illustrating a second operational configuration in which a nut is used to secure an elongate rod within the connecting portion of the implant, and also illustrating the removal of a portion of the implant body.

Referring now to FIGS. 5a, 5b, 6 and 7, shown therein is a spinal implant according to another form of the present invention. For the purpose of simplicity, the elements which correspond to common elements found in the spinal implant illustrated in FIGS. 1–4 are designated by the same reference numerals.

The spinal implant illustrated in FIGS. 5a, 5b, 6 and 7 extends along a longitudinal axis L and is generally comprised of a bone anchorage portion 1 and a connector portion 2 adapted for connection to the elongate rod 3. While the bone anchorage portion 1 and connector portion 2 include certain features that are similar to features found in the spinal implant illustrated in FIGS. 1–4, there are several distinct differences. For example, instead of being configured as a hook, the bone anchorage portion 1 is configured as a bone screw. Additionally, instead of defining internal threads, the opposing flanges 6, 6' each define a series of outer threads 23, 23'. Likewise, the axial and lateral portions 11, 13 also define a series of outer threads that are formed continuously with the outer threads 23, 23'. Although the lateral portion 13 is illustrated as including a central aperture 25 positioned in general alignment with the U-shaped channel 5, it should be understood that aperture 25 may be removed. Additionally, instead of being configured as a set screw, the fastener 4 is configured as a nut or ring 26 having internal threads which correspond to threads 23, 23' defined about the exterior of the opposing flanges 6, 6'.

In one embodiment of the present invention, the spinal implant illustrated in FIGS. 5a, 5b, 6 and 7 is used in association with an osteosynthesis device in the following manner. Similar to the spinal implant of FIG. 4, prior to implantation, the nut 26 is initially threaded onto the outer threads of lateral portion 13 of extension 10, but not so far as to cause the lower surface of nut 26 to extend beyond the lower surface of lateral portion 13. The elongate rod 3 is then inserted through the lateral opening 17 and into the U-shaped channel 5. The nut 26 is then be further threaded along the outer threads of the axial portion 11 of extension 10 until the nut 26 engages the elongate rod 3. The nut 26 is then threaded along the flanges 6, 6' until the rod 3 is tightly engaged against the bottom surface of channel 5.

Preferably, the nut 26 has a height that is sized such that when the rod 3 is engaged against the bottom of channel 5, the upper surface 27 of the nut 26 is positioned at or below the upper surface 12 of the opposing flanges 6, 6'. At this point, the extension 10 may be separated from the remainder of the implant, such as by fracturing the extension 10 at a location adjacent notch 15, to provide a relatively low profile spinal implant. Additionally, although not specifically illustrated in FIGS. 6 and 7, as discussed above with regard to set screw 4, nut 26 may be formed such that an upper portion of nut 26 is controllably and selectively separable from the remainder of nut 26.

Although not shown in FIGS. 5a, 5b, 6 and 7, a retention relief similar to relief 20 may be provided on the lower surface of lateral portion 13 to provide the lateral opening 17 with a width slightly less than the diameter of the elongate rod 3. In this manner, the rod 3 may be provisionally maintained within the inner channel of the spinal implant. Additionally, in an alternative embodiment of the invention, the spinal implant may be configured to allow the bone anchorage portion 1 to articulate relative to the connector portion 2 so as to permit a multi-axial angular orientation of the bone anchorage portion 1 relative to the connector portion 2.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal implant, comprising:
   a bone anchorage portion;
   a connector portion including first and second flanges extending axially from said anchorage portion and spaced apart to define a channel adapted to receive an elongate member therein;
   an extension portion including a first portion extending axially from said first flange and a second portion extending transversely from said first portion toward said second flange; and
   a fastener operable to advance along said first and second portions of said extension portion and into engagement with said first and second flanges to secure said elongate member within said channel.

2. The spinal implant of claim 1, wherein said extension portion is selectively separable from said connector portion.

3. The spinal implant of claim 2, wherein said first portion of said extension portion is integrally connected to said first flange of said connector portion by a fracture initiator, said fracture initiator permitting said extension to be selectively separated from said first flange by breaking.

4. The spinal implant of claim 3, wherein said fracture initiator is comprised of a notch formed along a surface of the implant between said connector portion and said extension portion.

5. The spinal implant of claim 2, wherein said fastener includes a lower portion and an upper portion, said upper portion being selectively separable from said lower portion.

6. The spinal implant of claim 1, wherein said fastener is a set screw.

7. The spinal implant of claim 1, wherein said transverse and axial portions of said extension portion and said first and second flanges of said connector portion define a continuous inner thread, said fastener being operable to threadingly advance along said continuous inner thread and into engagement with said elongate member.

8. The spinal implant of claim 7, wherein said transverse portion of said extension portion includes an axial opening having an uninterrupted inner surface, said continuous inner thread extending entirely about said uninterrupted inner surface.

9. The spinal implant of claim 8, wherein said fastener is threadingly engaged within said axial opening prior to implantation of the spinal implant.

10. The spinal implant of claim 7, wherein said fastener includes a lower portion and an upper portion, said upper portion being selectively separable from said lower portion, said lower portion being sized so as not to protrude beyond an upper surface of said first and second flanges when said fastener is engaged against said elongate member secured in said channel.

11. The spinal implant of claim 1, wherein said transverse and axial portions of said extension portion and said first and second flanges of said connector portion define a continuous outer thread, said fastener being operable to threadingly advance along said continuous outer thread from said transverse portion to said first and second flanges and into engagement with said elongate member.

12. The spinal implant of claim 11, wherein said fastener is a nut.

13. The spinal implant of claim 11, wherein said transverse portion of said extension portion includes an uninterrupted outer surface, said continuous outer thread extending entirely about said uninterrupted outer surface.

14. The spinal implant of claim 11, wherein said fastener is threadingly engaged with said transverse portion prior to implantation of the spinal implant.

15. The spinal implant of claim 11, wherein said fastener is sized such as not to protrude beyond an upper surface of said first and second flanges when said fastener is engaged against said elongate member secured in said channel.

16. The spinal implant of claim 1, wherein said second flange of said connector portion and said second portion of said extension portion cooperate to define a lateral opening in communication with said channel and adapted to receive said elongate member therethrough.

17. The spinal implant of claim 16, wherein said second portion includes a relief extending toward said second flange to define a minimum width of said lateral opening, said minimum width being less than an outer cross section of said elongate member.

18. The spinal implant of claim 17, wherein said extension portion is resiliently deformable between an initial configuration and a deformed configuration to vary said minimum width of said lateral opening, said deformed configuration permitting insertion of said elongate rod through said lateral opening.

19. The spinal implant of claim 17, wherein said relief extends from a lower lip of said second portion, said lower lip being deflectable to vary said minimum width of said lateral opening to permit insertion of said elongate rod therethrough.

20. A spinal implant, comprising:
a bone anchorage portion;
a connector portion coupled to said anchorage portion and adapted for connection to an elongate member;
an extension portion extending from said connector portion and being selectively separable therefrom; and
a fastener operable to advance along said extension portion and said connector portion and into engagement with said elongate member to connect said connector portion to said elongate member.

21. The spinal implant of claim 20, wherein said extension portion is integrally connected to said connector portion by a region of reduced strength.

22. The spinal implant of claim 21, wherein said region of reduced strength defines a fracture initiator to permit said extension portion to be selectively separated from said connector portion by breaking.

23. The spinal implant of claim 21, wherein said region of reduced strength comprises an area of reduced cross section.

24. The spinal implant of claim 23, wherein said area of reduced cross section is defined by a notch formed along an outer surface of the implant between said connector portion and said extension portion.

25. The spinal implant of claim 20, wherein said connector portion includes first and second flanges extending axially from said anchorage portion and spaced apart to define a channel adapted to receive the elongate member therein, said extension portion including a first portion extending axially from said first flange and a second portion extending transversely from said first portion toward said second flange; and
wherein said fastener is operable to advance along said first and second portions of said extension portion and into engagement with said first and second flanges to secure the elongate member within said channel.

26. The spinal implant of claim 25, wherein said transverse and axial portions of said extension portion and said first and second flanges of said connector portion define a continuous thread, said fastener being operable to threadingly advance along said continuous thread and into engagement with the elongate member.

27. The spinal implant of claim 26, wherein said transverse portion includes an uninterrupted surface, said continuous thread extending entirely about said uninterrupted surface to facilitate initial threading engagement with said fastener.

28. The spinal implant of claim 20, wherein said connector portion includes a first series of threads, said extension portion including a second series of threads in continuity with said first series of threads, said fastener being operable to threadingly advance along said first and second series of threads and into engagement with said elongate member to connect said connector portion to said elongate member.

29. The spinal implant of claim 28, wherein said fastener is a set screw, and wherein said first and second series of threads are formed along an inner surface of said connector portion and said extension portion.

30. The spinal implant of claim 28, wherein said fastener is a nut, and wherein said first and second series of threads are formed along an outer surface of said connector portion and said extension portion.

31. The spinal implant of claim 20, wherein said connector portion is formed of a metallic material and wherein said extension portion is formed of a non-metallic material.

32. The spinal implant of claim 31, wherein said extension portion is formed of a polymer.

33. The spinal implant of claim 20, wherein said fastener includes a lower portion and an upper portion, said upper portion being selectively separable from said lower portion.

34. The spinal implant of claim 33, wherein said upper and lower portions of said fastener are connected at a fracture initiating break line.

35. The spinal implant of claim 33, wherein said upper portion is fractured from said lower portion at a predetermined torque level.

36. The spinal implant of claim 33, wherein said upper portion of said fastener includes a first impression adapted to accept a driving tool, said lower portion of said fastener including a second impression adapted to accept said driving tool upon separation of said upper portion from said lower portion.

37. The spinal implant of claim 20, wherein said bone anchorage portion is configured as a hook.

38. The spinal implant of claim 20, wherein said bone anchorage portion is configured as a screw.

39. The spinal implant of claim 20, wherein said fastener is engaged to said extension portion prior to implantation of the spinal implant.

40. A spinal implant for an osteosynthesis device, comprising:
an anchoring portion adapted to engage bone;
a body portion adapted for fixation to an elongate rod, said body portion including:
a channel delimited by a pair of opposing side branches and sized to receive said elongate rod therein, said side branches defining a first threading; and
a continuation including a first portion extending axially from one of said side branches and a second portion extending laterally from said first portion toward another of said side branches, said continuation defining a second threading in continuity with said first threading; and
means for clamping said elongate rod within said channel, said means for clamping cooperating with said first and second threadings to advance said means for clamping along said body portion and into engagement with said elongate rod to clamp said elongate rod within said channel.

41. The spinal implant of claim 40, wherein said continuation is selectively separable from said one of said side branches.

42. The spinal implant of claim 41, wherein a notch is formed along an outer surface of the implant between said first portion of said continuation and said one of said side branches to provide an area of lessened resistance to facilitate separation of said continuation.

43. The spinal implant of claim 42, wherein said means for clamping comprises a threaded plug; and wherein said first threading is formed along inner surfaces of said first and second branches, said second portion of said extension defining an opening extending therethrough, said second threading being formed along said opening and along an inner surface of said first portion of said extension.

44. The spinal implant of claim 43, wherein said threaded plug includes a lower portion and an upper portion, said upper portion being separable from said lower portion.

45. The spinal implant of claim 40, wherein said means for clamping comprises an internally threaded ring; and wherein said first threading is formed along outer surfaces of said first and second branches, said second threading being formed along an outer surface of said first and second portions of said extension.

* * * * *